US00PP37213P3

(12) United States Plant Patent
Moucheboeuf

(10) Patent No.: US PP37,213 P3
(45) Date of Patent: Jan. 13, 2026

(54) ***DIANTHUS* PLANT NAMED 'WP24 JAP01'**

(50) Latin Name: ***Dianthus* x *allwoodii hort***
Varietal Denomination: WP24 JAP01

(71) Applicant: KLEMM + SOHN GMBH & CO. KG, Stuttgart (DE)

(72) Inventor: Laetitia Moucheboeuf, Exeter (GB)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/229,555

(22) Filed: Jun. 5, 2025

(65) Prior Publication Data

US 2025/0386748 P1 Dec. 18, 2025

(30) Foreign Application Priority Data

Jun. 12, 2024 (QZ) ..... PBR 2024/1319

(51) Int. Cl.
*A01H 5/02* (2018.01)
*A01H 6/30* (2018.01)

(52) U.S. Cl.
USPC ..... Plt./272

(58) Field of Classification Search
USPC ..... Plt./272
See application file for complete search history.

(56) References Cited

U.S. PATENT DOCUMENTS

PP21,162 P3 * 7/2010 Whetman ..... A01H 6/305 Plt./283

* cited by examiner

*Primary Examiner* — Susan McCormick Ewoldt

(74) *Attorney, Agent, or Firm* — Weatherly IP Solutions, LLC; James M. Weatherly

(57) ABSTRACT

A new *Dianthus* plant designated 'WP24 JAP01' particularly distinguished by a dark maroon flower color that progressively gets darker as the flowering season progresses with a more defined pattern; and a short plant habit, is disclosed.

2 Drawing Sheets

CROSS REFERENCE TO RELATED APPLICATION

This patent application claims the benefit of priority from Community Plant Variety Rights Certificate No. 2024/1319 as filed on Jun. 12, 2024, with the Community Plant Variety Office, the contents of which are incorporated herein by reference for all it teaches and discloses.

Genus and species: *Dianthus* x *allwoodii hort.*

Variety denomination: 'WP24 JAP01'.

BACKGROUND OF THE NEW PLANT

The present invention comprises a new and distinct variety of Dianthus, botanically known as *Dianthus* x *allwoodii* hort. and hereinafter referred to by the variety name 'WP24 JAP01'. 'WP24 JAP01' originated from an open pollination in 2011 in Ashcombe, Dawlish, United Kingdom between the proprietary female Dianthus variety 'JAP 08.01' (unpatented) and an unknown male variety. Seeds from the cross were collected from the female parent, planted and a young plant was selected by the inventor in Ashcombe, Dawlish, United Kingdom and named 'WP24 JAP01'. In September 2012, 'WP24 JAP01' was first vegetatively propagated by vegetative stem cuttings in Ashcombe, Dawlish, United Kingdom. 'WP24 JAP01' was found to reproduce true to type in successive generations of asexual propagation in Ashcombe, Dawlish, United Kingdom via stem cuttings.

SUMMARY

The following are the most outstanding and distinguishing characteristics of 'WP24 JAP01' when grown under normal horticultural practices in Ashcombe, Dawlish, United Kingdom.

1. Dark maroon flower color that progressively gets darker as the flowering season progresses with a more defined pattern; and
2. Short plant habit.

DESCRIPTION OF THE PHOTOGRAPHS

This new Dianthus plant is illustrated by the accompanying photographs of a 9-month-old plant taken in June 2020 and grown in a greenhouse in Dawlish, United Kingdom. The colors shown are as true as can be reasonably obtained by conventional photographic procedures.

Figure 1:
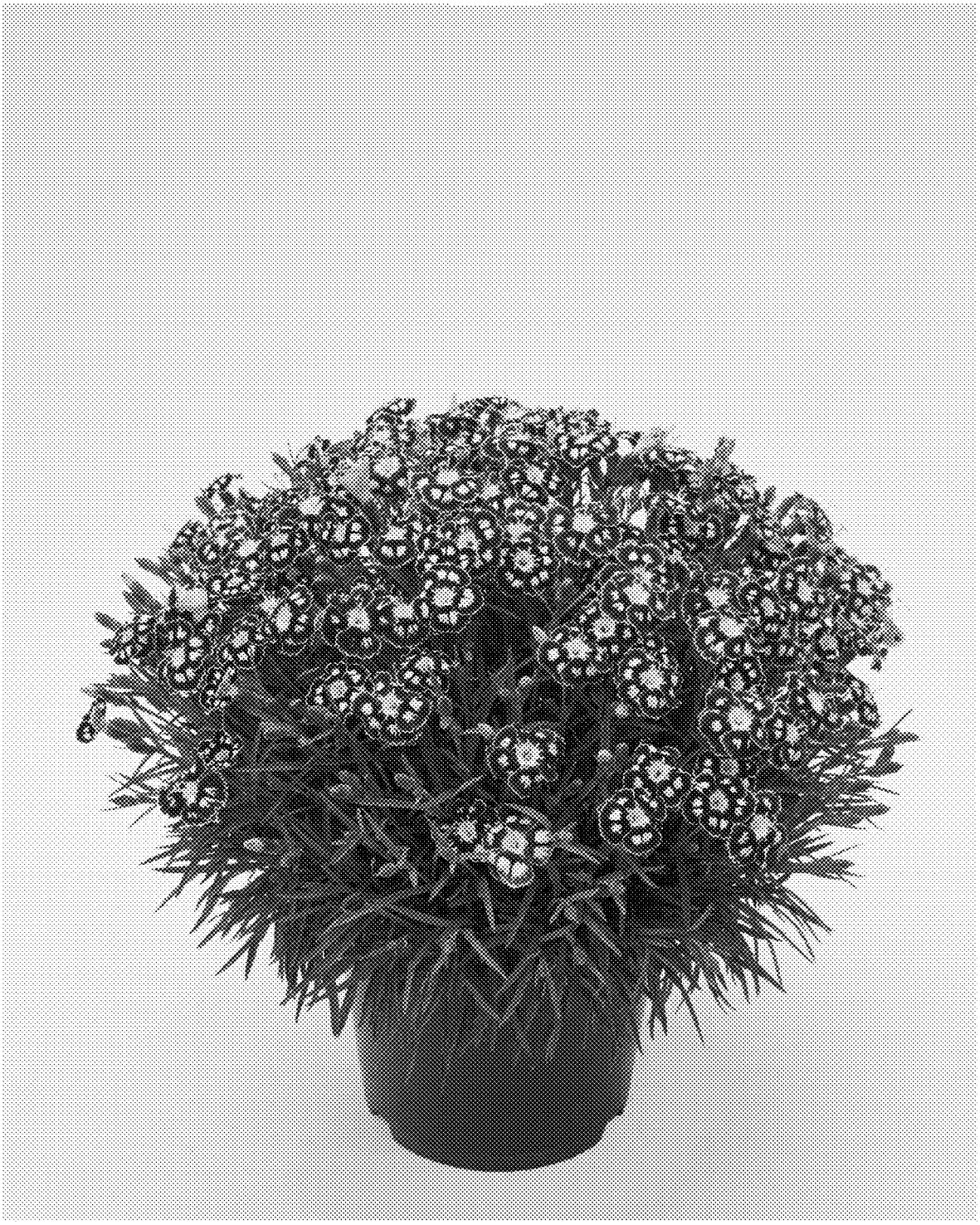

FIG. 1. The photograph is a whole plant photo of 'WP24 JAP01' and shows the foliage, buds, and flowers.

Figure 2:
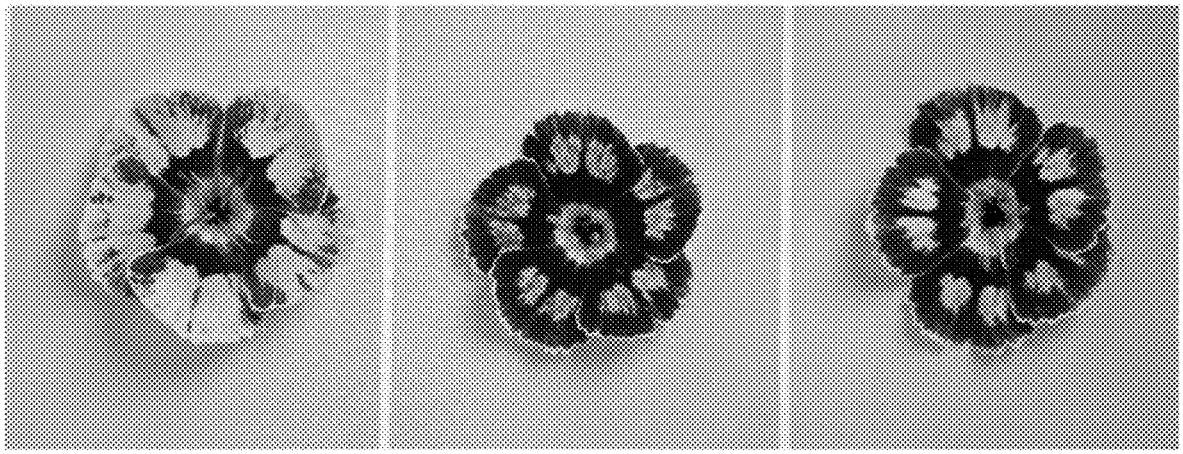

FIG. 2. The photograph shows the color transition of the flower color from the early flowering to the late flowering season.

DESCRIPTION

The following detailed descriptions set forth the distinctive characteristics of 'WP24 JAP01'. The data which define these characteristics were collected from asexual reproductions carried out in Ashcombe, Dawlish, United Kingdom.

Data was collected in April 2025 from eight-month-old plants in eleven centimeter pots. Color references are to The R.H.S. Colour Chart of The Royal Horticultural Society of London (R.H.S.), 6th edition (2015).

Classification:

*Family*.—Caryophyllaceae.

*Botanical*.—*Dianthus* x *allwoodii* hort.

*Designation*.—'WP24 JAP01'.

Parentage:

*Female parent*.—Dianthus 'JAP 08.01' (unpatented).

*Male parent*.—Unknown.

Propagation:

*Type*.—Vegetative via shoot cuttings.

*Time to produce a rooted young plant*.—5 weeks to produce a rooted plug.

*Root description* (*please include RHS*).—Fibrous, RHS 156D.

*Rooting habit*.—Fibrous.

Plant description:

*Plant form*.—Compact mounding habit.

*Plant height*.—15.0 cm to 17.0 cm.

*Plant diameter or spread*.—13.0 cm to 15.0 cm.

Lateral branches:

*Shape of the branch in cross-section*.—Circular.

*Hollowness of the branch*.—Absent.

*Length*.—7.0 cm to 9.0 cm.

*Diameter*.—0.3 cm to 0.4 cm.

*Internode quantity per branch*.—5.

*Number of internodes per branch/stem*.—5.

*Internode length*.—0.3 cm to 0.7 cm.

*Node length*.—0.3 cm.

*Node diameter*.—0.3 cm.

*Texture*.—Smooth.

*Color*.—Between RHS 144C and RHS 144D.

*Flower clustering on the lateral branch*.—None.

Foliage description:

*Arrangement*.—Opposite, sheathing and spiraling up the stem.

*Length*.—5.0 cm to 7.0 cm.

*Width*.—0.5 cm.

*Shape*.—Linear.

*Apex*.—Acute.

*Base*.—Decurrent.

*Margin*.—Entire.

*Texture*.—Upper surface: Smooth Lower surface: Smooth

*Cross-section of the leaf*.—Flat to very weakly concave.

*Curvature of the leaf*.—Absent.

*Glaucosity of the leaf*.—Strong.

*Venation pattern*.—Absent.

*Color*.—Immature leaves: Upper surface: Between RHS 138A and RHS 138B Lower surface: RHS 138B Mature leaves: Upper surfaces: Between RHS 189A and RHS 191A Lower surface: Between RHS 191A and RHS191B Flower description:

*Flower type and habit*.—Single, polypetalous

*Fragrance*.—Present, medium.

*Position of the flowers compared to the foliage of the plant*.—Moderately above.

*Profile of both the upper and lower part in the lateral view*.—Flat, concave.

*Diameter of the flower*.—3.5 cm to 4.0 cm.

*Natural flowering season*.—May to October.

*Number of flowers per spray*.—3 to 4.

*Flower longevity on the plant*.—10 days at 20° Celsius on the plant; 8 to 10 days off the plant.

Flower buds:

*Length*.—1.7 cm to 1.9 cm.

*Diameter*.—0.5 cm to 0.7 cm.

*Shape*.—Cylindrical.

*Color*.—Between RHS N138B and RHS 138C on the apical half, between RHS 144C and RHS 144D on the basal half (under the bracts).

*Extrusion of the styles at the bud stage*.—Absent.

Corolla:

*Quantity of petals/arrangement*.—5 petals, persistent, apopetalous and overlapping.

*Corolla height*.—2.0 cm.

*Petal length*.—2.0 cm to 2.2 cm.

*Petal width*.—3.5 cm to 4.0 cm.

*Petal shape*.—Fan.

*Petal apex*.—Fan shaped, crenate-dentate.

*Petal base*.—Strap shaped, tapering towards the base.

*Petal margin*.—Crenate-dentate.

*Depth of petal margin*.—Shallow.

*Petal texture*.—Upper surface: Smooth Lower surface: Smooth

*Immature petals*.—Early flowers initiated in Spring when the temperatures are cooler have a lighter main color, less in proportion compared to the main season flowers, and the clock pattern is not as well defined Color: Upper surface: Between RHS 61A and RHS 67 A in the macule zone and between RHS 69A to RHS 69D in the patches and petal edges Lower surface: RHS N155B Macule color RHS 61A and RHS 67A are present (overall the color is more towards the pink/purple) Patches colour and petal edges: RHS 69A to RHS 69D

*Mature petals*.—As the season progress the flower color is getting darker, and the pattern is more defined and consistent. Color: Upper surface: The main color RHS 59A and RHS 60A with the background RHS 69D. Lower surface: RHS N155B Pattern description: Macule expanding into towards the apex of the petal through the middle of the petal and across the apex, joining back towards the macule. Two zones, patch like, of a light pink colour makes the impression of a clock pattern. Macule color: RHS 59A and RHS 60A Size: 0.4 cm Patches colour and petal edges RHS 69D fading towards white as flower ages.

Calyx:

*Quantity of sepals/arrangement*.—5, fused up to 0.5 cm below the apex.

*Longitudinal axis of the lobes of the calyx*.—Straight.

*Shape*.—Cylindrical.

*Calyx height*.—2.0 cm.

*Calyx diameter, at the apex*.—0.6 cm.

*Sepal texture*.—Upper surface: Smooth Lower surface: Smooth

*Sepal color*.—Upper surface: Between RHS N138B and RHS 138C Lower surface: Between RHS 144C and RHS 144D

*Position of the outer lobes of the epicalyx in relation to the calyx*.—Adpressed.

*Apex shape of the outer lobes of the epicalyx*.—Adpressed and short acuminate.

*Tip length of the outer lobes of the epicalyx*.—0.5 cm to 0.7 cm.

*Apex shape of the inner lobes of the epicalyx*.—Free and acute.

*Tip length of the inner lobes of the epicalyx*.—0.4 cm to 0.6 cm.

Peduncles:

*Length*.—11.0 cm to 13.0 cm.

*Diameter*.—0.2 cm.

*Strength*.—Strong.

*Texture*.—Smooth.

*Color*.—Closest to RHS 122B.

Reproductive organs:

*Stamens*.—Quantity: 10 Filament length: 2.1 cm to 2.3 cm Filament color: RHS NN155D Anther length: 0.2 cm Anther diameter: 0.1 cm Anther color: Between RHS 77C and RHS 77D (before dehiscence) Pollen amount: Present, between RHS 202C and RHS 202D

*Pistils*.—Quantity: 1 (2 styles) Pistil length: 3.0 cm to 3.5 cm Style length: 2.0 cm to 2.5 cm Style color: RHS NN155D Stigma shape: Linear and hairy, along the style, ending by 2 lobes Stigma color: Between RHS N78C and RHS 78D Ovary size: 0.8 cm to 0.9 cm in length, 0.4 cm in diameter. Ovary shape: Oblong Ovary color: RHS 144C on the apical half and RHS 144D on the basal half.

Seeds: Present.

*Size*.—0.4 cm in length, 0.3 cm in width.

*Color*.—RHS 202A.

*Shape*.—Oval and flattened.

*Amount of seed*.—medium.

Disease and insect resistance: No particular disease or insect resistance observed.

COMPARISON OF 'WP24 JAP01' WITH PARENTAL LINES AND KNOWN VARIETY

'WP24 JAP01' is distinguished from the parents as described in Table 1.

TABLE 1

| Comparison with Parental Line | | |
|---|---|---|
| Characteristic | 'WP24 JAP01' | Female parent |
| Flower Type | Single | Semi-double |
| Plant Height | Short | Tall |

'WP24 JAP01' can be compared to the commercial Dianthus variety 'Starburst' (U.S. Plant Pat. No. 21,162). Differences between the varieties are described in Table 2.

TABLE 2

| Comparison with Similar Variety | | |
|---|---|---|
| Characteristic | 'WP24 JAP01' | 'Starburst' |
| Flower Type | Single | Semi-double |
| Flower Color | Darker maroon range | Light pink range |

I claim:

1. A new and distinct variety of Dianthus plant designated 'WP24 JAP01' as illustrated and described herein.

* * * * *